United States Patent
Watanabe

(10) Patent No.: US 6,376,238 B1
(45) Date of Patent: Apr. 23, 2002

(54) CULTURE MEDIA FOR NEURONS, METHODS FOR PREPARING THE CULTURE MEDIA, AND METHODS FOR CULTURING NEURONS

(75) Inventor: Yoshiaki Watanabe, Akita (JP)

(73) Assignee: Sumitomo Bakelite Co., Ltd., Tokyo (JP)

( * ) Notice: Subject to any disclaimer, the term of this patent is extended or adjusted under 35 U.S.C. 154(b) by 0 days.

(21) Appl. No.: 08/776,525

(22) PCT Filed: Jun. 26, 1996

(86) PCT No.: PCT/JP96/01764

§ 371 Date: Feb. 27, 1997

§ 102(e) Date: Feb. 27, 1997

(87) PCT Pub. No.: WO97/01628

PCT Pub. Date: Jan. 16, 1997

(30) Foreign Application Priority Data

Jun. 27, 1995 (JP) ............................. 7-160382
Feb. 28, 1996 (JP) ............................. 8-040889
Jun. 10, 1996 (JP) ............................. 8-147158

(51) Int. Cl.$^7$ ............... A01N 63/00; A01N 65/00; C12N 5/00; C12N 5/02
(52) U.S. Cl. ............ 435/325; 424/93.7; 424/520; 424/570; 435/404; 435/407; 435/408
(58) Field of Search .................. 435/240.3, 325, 435/352, 378, 384, 388, 389, 392, 405, 407, 948, FOR 100, FOR 101, FOR 102, FOR 13, 7.1, 404, 408; 424/93.7, 520, 570

(56) References Cited

U.S. PATENT DOCUMENTS 5,438,121 A * 8/1995 Barde et al. ............... 530/399
5,565,436 A * 10/1996 Kawagishi et al. ......... 514/33
5,714,385 A * 2/1998 Mather et al. ............. 435/406
5,721,139 A * 2/1998 Mather et al. ............. 435/383
5,898,066 A * 4/1999 Benowitz et al. .......... 530/300
5,935,795 A * 8/1999 Lin et al. .................. 435/7.1

FOREIGN PATENT DOCUMENTS

JP 5-111381 5/1993
JP 5-227278 8/1995

OTHER PUBLICATIONS

N. Yamashita et al, "Primary culture of postnatal rat hypothalamic neurons in astrocyte–conditioned medium", Brain Research, vol. 594, pp. 215–220, 1992.

F. Kawahara et al, "Primary culture of postnatal rat suprachiasmatic neurons in serum–free supplemented medium", Brain Research, vol. 651, pp. 101–107, 1994.

* cited by examiner

*Primary Examiner*—Michael G. Wityshyn
*Assistant Examiner*—Deborah K. Ware
(74) *Attorney, Agent, or Firm*—Oblon, Spivak, McClelland, Maier & Neustadt, P.C.

(57) ABSTRACT

The present invention is directed to a culture medium for neurons prepared by adding albumin to a culture supernatant obtained from a culture of primary astroglial cells in a trophic medium supplemented with insulin and transferrin. The culture medium of the present invention makes it possible to culture central nerve cells consistently. When nerve cells are cultured at a low cell density, excellent neurite extension is obtained, and synapses are formed rapidly. On the other hand, when nerve cells are cultured at a high cell density, long-term stability of cells that have formed neuronetworks can be obtained.

19 Claims, No Drawings

CULTURE MEDIA FOR NEURONS, METHODS FOR PREPARING THE CULTURE MEDIA, AND METHODS FOR CULTURING NEURONS

TECHNICAL FIELD

The present invention relates to a culture media for culturing neurons, to methods for preparing the culture media, and to methods for culturing neurons by use of the culture media.

DESCRIPTION OF THE RELATED ART

In order to culture neurons ex vivo, many studies have been conducted since long ago. The discovery of the nerve growth factor (NGF), being the first discovery of a factor that specifically functions on neurons, was epoch-making in the field of neurobiology. In culturing neurons, NGF has made it possible to induce growth of nerve fibers, and accordingly, neurons have come to be cultured under conditions more closely resembling in vivo.

Recently, new nerve growth factors such as ciliary neurotrophic factor (CNTF), brain-derived neurotrophic factor (BDNF), neurotrophic factor-3 (NT-3), neurotrophic factor-4 (NT-4), neurotrophic factor-5 (NT-5), and glial cell line derived neurotrophic factor (GDNF) have been discovered one after another. These factors have been studied with respect to their effects and functional mechanisms by use of cultured neurons, and have now come to the stage where use thereof as medicines for the treatment of diseases is being considered through the application of genetic engineering techniques that have been put into practice.

However, when these factors are investigated in an ordinary culture system for central nerve cells, a disadvantage is encountered in that a plurality of substances must be added in order for a significant effect to be obtained for various neurons; i.e., when a single substance is added, effect is observed on only certain specific cells.

Regarding culturing of central nerve cells, there has been an another approach in which use of hormones (insulin, thyroxine, progesterone, etc.), vitamins, unsaturated fatty acids, and growth factors (such as basic fibroblast growth factor) has been studied. Serum-free culture media in which these substances are combined differently have heretofore been reported [Journal of Neuroscience Methods, 23:75 (1988), etc.]. Although these culture media are effective toward certain cell lines (such as the glial cell line), there are cases in which neurons cannot be stably cultured, or in which the culture media are effective toward neurons but proliferation of glial cells is simultaneously stimulated, to thereby render the culture system a so-called mixed culture system involving glial cells in addition to neurons. This is detrimental, particularly when pharmacological action on neurons is to be studied. For example, although the N2 supplement of Bottenstein et al. [insulin (5 $\mu$g/ml), transferrin (100 $\mu$g/ml), progesterone (20 nM), putrescine (100 $\mu$M), and selenious acid salts (30 nM); Proceeding of National Academy of Science, U.S.A., 76:514(1979)] is suitable for culturing glial cell lines, it cannot stably maintain viable primary neurons. Also, the culture medium disclosed by Brewer et al. [Brain Research, 65:494(1989)] cannot stably maintain cellular functions when used for long-term culturing, although it permits short-term culturing of central nerve cells.

In the meantime, it is known that a culture supernatant of a glial cell line or primary glial cells is used for culturing neurons. When a culture supernatant of a glial cell line is used, it is generally unavoidable that the supernatant acts not only on neurons but also on glial cells to thereby stimulate the proliferation of glial cells. In other words, although the culture supernatant is effective in maintaining survival of neurons, it exhibits much greater effects on glial cells. A so-called glial cell growth factor has been purified from these culture supernatants [Journal of Biological Chemistry, 268: 2857 (1993), etc.].

In addition, Japanese Patent Application Laid-Open (kokai) No. 7-101990 discloses that a concentrated culture supernatant of astrocytoma, which is a type of glial cell lines, exhibits 30–50% elevation in activity of cultured neurons. In that publication, it is also disclosed that the concentrate suppresses proliferation of neuroblastoma. The technique of that publication is significant in that a culture supernatant is concentrated to take up part of active components so as to suppress proliferation of glial cells, which proliferation is the drawback involved in use of a culture supernatant of a glial cell line. However, in order to stably and consistently culture neurons, collective action of a plurality of components is required rather than the action of a single substance. A stable culture system for neurons cannot be established through elevation in activity as low as 30% relative to the case in which the concentrate is not used.

In a method in which primary glial cells are used, an ordinary serum-free culture medium is employed, or serum-containing culture medium is used to obtain a culture supernatant. When an ordinary serum-free culture medium is used to obtain a culture supernatant, the culture medium does not satisfactorily promise viability of glial cells, and therefore, stable culturing cannot be realized. Consequently, the amount of factors (substances) that act on the neurons present in the culture supernatant becomes small, to thereby exhibit only an insignificant effect in culturing of neurons. Moreover, collection of a culture supernatant may be performed in limited numbers, and after several times of collection, it becomes difficult to collect a culture supernatant that provides a stable effect. On the other hand, when a serum-containing culture medium is used, a culture supernatant can be collected in a stable manner. However, when neurons are cultured, the growth factor acts on glial cells rather than on co-existing neurons, to thereby stimulate proliferation of cells. As a result, stable culturing of neurons is hampered.

Generally, serum-free culture media are supplemented with trophic factors such as hormones. For example, Japanese Patent Application Laid-Open (kokai) No. 3-66700 discloses a culturing method in which Dulbeccol's modified Eagle medium (hereinafter referred to as DMEM) is supplemented with insulin (5 $\mu$g/ml), transferrin (1 $\mu$g/ml), hydrocortisone (20 nM), and 3,3',5-triiodo-L-thyronine (0.3 nM). However, when this culture supernatant is used for the culturing of neurons, stable culturing cannot be achieved beyond a period of several days. Also, $\alpha$2-macroglobulin—which is explicitly described in that publication as a neurite-outgrowth promoting factor—exhibits insignificant effect on achieving stable culturing for central nerve cells, and thus plays only an auxiliary role, not a principal role.

Japanese Patent Application Laid-Open (kokai) No. 3-155777 discloses that a certain factor produced by microgliacytes is effective for neurite-outgrowth. Microglia is said to exhibit a function analogous to lymphocyte such as macrophage, and their activity elevates when tissue is injured. However, it is accepted that macroglias—including astroglial cells—are predominantly present in living bodies in general, and that it is principally macroglias that maintain homeostasis except in special cases such as inflammation.

The above-described conventional culture media are not sufficiently effective when they are used to culture central nerve cells, and therefore, consistent culturing of neurons cannot be achieved. In other words, satisfactory results as expected cannot be obtained through use of conventional culture media in neuropharmacological tests. Accordingly, the present invention was made in view of the foregoing circumstances in relation to culturing of neurons, and objects of the invention are to provide culture media that are capable of consistently culturing neurons for long periods.

DISCLOSURE OF THE INVENTION

Based on the idea that the presence of a variety of trophic factors must be required for consistent culturing of neurons, the present inventors investigated how trophic factors affect culturing of neurons. They also examined a culture supernatant of primary astroglial cells as one of the trophic factors. As a result, the trophic factors they examined were found to provide insufficient effects when used independently and solely. Particularly, it was found that the culture supernatant of primary astroglial cells was in fact not as effective as had been reported toward consistent culture of neurons. Therefore, the present inventors initiated investigations of combination effects and synergetic effects through use of a plurality of trophic factors, and conducted careful studies on different effects of culturing, thus leading to completion of the present invention.

Accordingly, the present invention provides culture media for neurons characterized by comprising (A) a culture supernatant obtained from a culture of primary astroglial cells in a trophic medium supplemented with insulin and transferrin, and (B) albumin.

The present invention also provides a method for preparing the above-described culture medium for neurons characterized by culture and proliferation of primary astroglial cells in a medium supplemented with animal serum, and culturing in a trophic medium supplemented with insulin and transferrin, then collection of a supernatant of the culture, and addition of albumin to the obtained culture supernatant.

The present invention further provides a method for culturing neurons characterized by culturing neurons in the above-described culture media for neurons.

BEST MODE FOR CARRYING OUT THE INVENTION

In order to prepare a culture medium for neurons, astroglial cells are collected from the animal brain. The collected astroglial cells—primary astroglial cells—are proliferated until they come to be in sufficient amounts. The astroglial cells are preferably collected from the cerebrums of newborn animals (1–2 days old). Animals suitable for the collection of astroglial cells include rats, mice, bovines, horses, pigs, monkeys, rabbits, and hens, with rats and mice being particularly preferred.

Briefly, the cerebrum is excised out of the brain of a newborn, and after the cerebral meninges is removed therefrom, the cerebrum cells are dissociated through use of enzymes such as trypsin, disperse, collagenase, and papain. Use of 0.05–0.35 w/v % (hereinafter simply referred to as %) trypsin is particularly preferred. It is also effective to add, to trypsin, 0.01% (100–500 U/ml) deoxyribonuclease or 0.01% ethylenediamine-N,N,N',N'-tetraacetic acid (EDTA). The collected astroglial cells are preferably cultured and proliferated in a medium containing animal serum. The animal serum is preferably bovine serum, and more preferably, fetal calf serum, calf serum, or neonatal calf serum. The amount of animal serum to be added is preferably in the range of 5–20%. The medium is not particularly limited so long as it is a trophic medium for culturing animal cells. Examples of such medium include Eagle's minimum essential medium (hereinafter abbreviated as MEM), Dulbecco's modified Eagle medium (hereinafter abbreviated as DMEM), DMEM/HAM's F-12 medium (hereinafter abbreviated as F-12), F-12, and HAM's F-10 medium (hereinafter abbreviated as F-10). Although the mixing ratio of DMEM to F-12 in DMEM/F-12 media may vary, the ratio be preferably in the range from 60/40 to 40/60 (on a weight basis) so that the resultant media have the traits of both media.

The astroglial cells dispersed in a culture medium are cultured until confluency through use of a flask, a dish, or a plate—all of which are used for cell culture—or a polylysine-coated flask, a polylysine-coated dish, a polylysine-coated plate, or a polylysine-coated microcarrier. The culture area is preferably 10–100 $cm^2$ with respect to one newborn animal. Subsequently, subculturing is performed until confluency. In subculturing, a culture area of 2–10 times is preferred. The cells that reached confluency are mainly those categorized as type 1 astroglial cell (or type 1 astrocyte). That the cells are type 1 astroglial cell is confirmed by immunocytochemical staining. The cells are stained with anti-GFAP (GFAP: glial fibrillary acidic protein) antibody, but are not stained with anti-A2B5 antibody (anti-sialosyl glycoprotein antibody).

When the cells reach confluency, the culture medium is discarded and the residue is washed with phosphate buffered saline, etc.

The thus-obtained primary astroglial cells are cultured in a trophic medium supplemented with insulin and transferrin, and their supernatant is collected. Trophic media which may be used herein may be one or more members selected from the group consisting of MEM, DMEM, F-10, and F-12. Preferred media are MEM, DMEM, DMEM/F-10 and DMEM/F-12, with DMEM/F-12 being particularly preferred. The preferred ratio of DMEM to F-12 is 60/40–40/60 (on a weight basis).

These trophic media are supplemented with insulin and transferrin. Preferably, selenious acid or a salt thereof is additionally incorporated. Insulin is added in an amount so as to achieve an insulin concentration of 1–100 $\mu$g/ml, and preferably 3–20 $\mu$g/ml. Transferrin is added in an amount so as to achieve a transferrin concentration of 1–100 $\mu$g/ml, and preferably 3–20 $\mu$g/ml. Examples of salts of selenious acid include sodium selenite and potassium selenite. It is preferred that selenious acid or a salt thereof be added in such an amount that will make its concentration 1–100 nM; particularly preferably 3–50 nM. All of insulin, transferrin, and salts of selenious acid are water-soluble, and therefore, they may be incorporated as they are. It is also an advantageous approach that a solution containing any of these components at a high. concentration is prepared in advance and a certain amount thereof is incorporated.

The culture period is as short as one day. If a new medium and supplements are replenished after supernatant has been collected to thereby perform culture, supernatant can be collected repeatedly. In this way, supernatant can be collected every day for more than 10 times (days) up to 15 times (days) for a single preparatory operation of primary astroglial cells.

The culture supernatant thus collected is preferably used after being sterilized by being passed through a filter having pores of 0.02–0.45 $\mu$m to thereby remove cell debris.

When the culture supernatant alone is used as a culture medium, neurons cannot be cultured stably. Stable culture is possible only after albumin is added to the culture medium. Preferably, progesterone is also added in addition to albumin. The amount of albumin to be incorporated is preferably such that will make the albumin concentration 0.5–2.5 mg/ml. The amount of progesterone is preferably such that will make the progesterone concentration 1–100 nM.

When it is found that the concentration of insulin, transferrin, or selenious acid or a salt thereof is excessively low, it is preferred that these components be added so as to adjust the concentration of insulin to 1–100 μg/ml, that of transferrin to 1–100 μ/ml, and that of selenious acid or a salt thereof to 1–100 nM.

Preferably, the culture supernatant additionally contains a combination of superoxide dismutase and catalase and/or α-tocopherols. Preferred concentrations of these supplements are 1–100 μg/ml for superoxide dismutase, 1–100 μg/ml for catalase, and 1–100 μg/ml for α-tocopherols. Examples of α-tocopherols include α-tocopherol and esters of α-tocopherol such as tocopherol acetate and tocopherol succinate.

When culture media supplemented with albumin and other supplements as described above are used, neurons can be cultured in a consistent manner. Also, the culture media of the invention successfully overcome the problem of unstable culture which cannot be avoided when low-density culture is performed with previous culture media.

To the culture media may be newly added any of the aforementioned media as a trophic source for neurons. An example of such media is a DMEM/F-12 medium mixture. The medium is preferably added so as to achieve an amount of 0–75%, and particularly preferably 0.1–50%.

Examples of particularly preferred combinations of supplements include the following: albumin, progesterone, insulin, transferrin, and selenious acid (or a salt thereof); these five species plus α-tocopherols; the five species plus superoxide dismutase and catalase; the five species plus α-tocopherols, superoxide dismutase and catalase; and any of these combinations plus a DMEM/F-12 medium mixture.

In order to incorporate the above-described supplements into a culture supernatant, a method similar to that described above may be used if water-soluble progesterone and water-soluble α-tocopherol are used for progesterone and α-tocopherol, respectively. That is, a highly concentrated solution containing the additives may be prepared in advance and added. If water-insoluble progesterone and water-insoluble α-tocopherol are used, they are dissolved in ethanol in advance.

A culture supernatant can be stored stably in a frozen state. Therefore, in the case in which supernatants are collected every day consecutively, the supernatant collected each time is frozen without being combined with supplements such as insulin; and after a plurality of supernatants have been collected and frozen, they are thawed, uniformly mixed, and then combined with the supplements. This procedure provides more uniform culture media for neurons. It is preferred that the supplements in this case be prepared into a solution state before being added.

The supplements are stably stored if dissolved in pure water or in an aqueous solution such as phosphate buffered saline and then frozen. Progesterone, α-tocopherol, and other water-insoluble components are stored in a frozen state after they are dissolved in ethanol, etc. Also, the culture media of the present invention prepared as described above can be stably stored in a frozen state. The temperature at which any of culture supernatant, supplements, and blended culture media are stored in a frozen state is preferably between −10 and −80° C. If the storage temperature is that of a typical refrigerator (4–8° C.), it is difficult to store them stably for long periods. Preferably, a cycle of freezing and thawing should not be repeated.

In order to culture neurons through use of the culture media of the present invention, neurons are added to the culture media and a conventional culture procedure is performed. Neurons can be prepared by use of the animals similar to those from which primary astroglial cells are prepared. Although culture is possible with neonatal individuals, viability of neurons is generally improved when fetal animals are used. If rats are used, embryos of 15–20 days old are preferred. It is also possible to use more immature embryos. Moreover, neurons in limited regions of the brain, such as hippocampus, corpus striatum, septum, midbrain, or cerebellum may be cultured. When neurons in the cerebellum are desired to be cultured, good results can be obtained through use of neonatal individuals of approximately 1 week old in accordance with the differentiation of neurons.

In the case in which the brain is treated with an enzyme so as to dissociate neurons, glial cells (such as primary astroglial cells) are generally included in addition to neurons. Astroglial cells are categorized as type 1 and type 2, and when serum-added culture media are concerned, type 1 astroglial cells are grown to cause a problem. The culture media of the present invention are effective in suppressing the proliferation of these cells. Although types 1 and 2 astroglial cells cannot be definitely distinguished from each other based on the shape of primary astroglial cells, they are distinguished through use of immunocytochemical staining. Both types 1 and 2 are stained with anti-GFAP antibody, but only type 2 is stained with anti-A2B5 antibody. This difference in staining property can distinguish these two types of astroglial cells.

When the fetus brain is used, the proportion of undifferentiated cells is significant. The culture medium of the present invention induces proliferation and differentiation of oligodendroglia (or oligodendrocyte)—type 2 astroglia (or type 2 astrocyte) stem cells (hereinafter referred to as O-2A stem cells), which are one type of the undifferentiated stem cells. When incubation is continued, oligodendroglias—which are initially not observed—will come to be observed in the culture system. They are O-2A stem cells that have been proliferated and differentiated. The fact that the cells are oligodendroglias can be confirmed by use of similar immunocytochemical staining that is used for distinguishing astroglial cells. For example, when anti-GC (galactocerebroside) antibody, anti-MBP (myelin basic protein) antibody, etc. are used for staining, the oligodendroglia can be clearly distinguished.

A specific example of a culture method for neurons is as follows. The brain is removed in a manner similar to that as described above. A neuron dissociation is prepared through use of an enzyme such as trypsin, papain, or disperse. Preferably, papain (10–50 U/ml) is used. Lcystein (0.5–5 mM) and glucose (5–50 mM) are added to phosphate buffered saline in which papain has been dissolved. The brain tissue is enzymatically treated with the resultant solution at 37° C. for 30–120 minutes. The enzymatic solution is carefully stirred and mixed to thereby disperse the neurons. If deoxyribonuclease (0.01%) is further added, there can be prevented agglutination of cells due to the presence of nucleic acid that has been leached.

Subsequently, cells are separated by use of a centrifugal separator. The separated cells are added to the culture media of the present invention prepared as described above so as to prepare a cell suspension of 10,000–2,000,000 cells/ml. The cell suspension is placed in a culture plate or a culture dish and is cultured in a 5% $CO_2$ gas incubator at 37° C. The material of the plate, dish, etc. is not particularly limited, and may be glass, plastic, etc. Preferably, the plate or dish is coated with a single layer or a plurality of layers of polylysine, polyornithine, polyallylamine, protamine, laminin, collagen, gelatin, fibronectin, vitronectin, tenascin, or a mixture of them.

EXAMPLES

The present invention will next be described in more detail by way of examples, which should not be construed as limiting the invention thereto.

Example 1 and Comparative Examples 1 and 2

(1) Preparation of a Culture Medium

The cerebrums removed from the brains of three neonatal Wistar rats (1 day old) were enzymatically treated with 0.25% trypsin/phosphate buffered saline (Flow Laboratories) for 30 minutes at 37° C. The enzyme-containing solution was discarded, and the tissue cells were dissociated in a DMEM/F-12 (1:1) culture liquid mixture containing 10% fetal calf serum (Hiclone Co.) and 50 μg/ml of gentamicin (Sigma Co.). The resultant dissociation was centrifugally separated by use of a centrifugal separator for separating cells (Kubota K.K.) at 900 rpm for 5 minutes to thereby obtain cells.

The cells thus separated were combined with 15 ml of a culture medium having the same composition as described above, placed in a 75 $cm^2$ culture flask (Sumitomo Bakelite K.K.), and cultured in a 5% $CO_2$ incubator at 37° C. for 10 days. The culture medium was discarded, and the cells grown to confluency in the flask were washed with phosphate buffered saline. Subsequently, the cells were enzymatically treated with 0.25% trypsin/phosphate buffered saline for 5 minutes at 37° C. A culture medium having the same composition as described above (150 ml) was added to thereby dissociate the cells, and the dissociated cells were centrifugally separated in a manner similar to that described above. The separated cells were re-dispersed in a culture medium (150 ml), dispensed into three 225 $cm^2$-culture flasks (Sumitomo Bakelite K.K.), and cultured for 10 days. The culture media were replaced with fresh media every 2–3 days.

The culture medium in each flask was discarded, and the cells were washed twice with phosphate buffered saline. Subsequently, a DMEM/F-12 (1:1) culture medium mixture supplemented with insulin (5 μg/ml), transferrin (5 μg/ml), and sodium selenite (5 nM) (all by Sigma Co.) was added to the cells, and the cells were incubated for 1 day. The entirety of the culture supernatant was collected, and in place thereof, a culture medium having the same composition as described above was added. This procedure was repeated for 10 days (a total of 10 times). In Comparative Example 1, culture supernatants were collected in a manner similar to that described above except that the mentioned supplements were not added. The amount of the culture medium can be increased or decreased as desired depending on the shape of the culture substratum. Preferably, the amount of the culture media per culture area is between 0.15 and 0.35 $ml/cm^2$ when plates, flasks, dishes, or trays are used.

The culture supernatants thus collected were respectively filtered through 0.22 μm filters (Millipore Co.) and sterilized, and then stored in a frozen state. After 10 supernatants were collected and frozen, they were unified, thawed, and uniformly mixed. The resultant mixture was added to albumin (ALBUMAX™ I, Life Technology Co., 2.5 mg/ml), and stored at −70° C.

(2) Culture Test of Neurons

Neuron samples were prepared as follows: The cerebrums of rats (17 days old embryos) were enzymatically treated with papain (Worthington Co.) which had been prepared to have a concentration of 20 U/ml through use of phosphate buffered saline containing 1 mM cysteine, 25 mM glucose, and 1 mg/ml albumin (all by Sigma Co.) for 45 minutes at 37° C. The enzyme-containing solution was removed, and the cells were dissociated in a DMEM/F-12 culture medium mixture. Subsequently, the cells were centrifugally separated at 700 rpm for 5 minutes.

The culture medium of the present invention obtained in step (1) above was used to prepare a cell suspension having a cell concentration of 600,000 c/ml. The cell suspension was dispensed in the wells of a polylysine-coated 24-well plate (Sumitomo Bakelite K.K.) (0.5 ml/well) and cultured. In Comparative Example 2, culture was performed under the conditions described above through use of a DMEM/F-12 (1:1) culture medium mixture to which the culture medium of the present invention had not been added.

After the cells were cultured for 4 days, their morphology was observed under a microscope. The cells that were cultured in a culture medium to which the culture media of the present invention had been added survived in excellent condition, and exhibited elongated outgrowth of neurites. Also, a considerable number of contacts were observed between neurites that formed synapses. In contrast, the cells that were cultured through use of the culture medium of Comparative Example 1 were found to exhibit significantly poorer outgrowth of neurites, and many cells had shapes that indicated death of cells. In the case in which the culture medium of Comparative Example 2 was used, no living cells were observed.

In order to obtain the ratio of the number of living cells to that of dead cells, fluorescein diacetate (Sigma Co., 10 μg/ml) and propydium iodide (Sigma Co., 15 μg/ml) which had been dissolved in phosphate buffered saline added to the culture medium to react. The number of living cells and that of dead cells were counted under a fluoresence microscope (Olympus Optical), on the basis of the difference in fluorescence. As a result, it was found that the viability of the cells that were cultured in a culture medium to which the culture medium of the present invention had been added was very good and was 80% or higher.

Example 2 and Comparative Example 3

The procedure of Example 1 was repeated to culture primary astroglial cells and to collect culture supernatants. The collected culture supernatants were mixed with a DMEM/F-12 culture medium mixture in different ratios (supernatant/culture liquid mixture=75/25, 50/50, 25/75, and 10/90). To the total amount of each resultant solution, progesterone (20 nM) and albumin (2.5 mg/ml) (both by Collaborative Research Co.) were added as supplements so as to prepare a culture medium. In Comparative Example 3 was employed a culture medium which had been prepared by adding 10% of fetal calf serum (Hyclone Co.) to a DMEM/F-12 culture medium mixture. In a manner similar to that described in Example 1, a neuron suspension having a concentration of 500,000 c/ml was prepared and cultured as described in Example 1.

The cells were observed under a microscope after they were cultured for 4 days. The culture media in which the ratios of culture supernatant to DMEM/F-12 mixture medium were 75/25 and 50/50 exhibited excellent viability of neurons and outgrowth of neurites. The 25/75 culture medium showed a slightly smaller number of living cells. Both the number of living cells and outgrowth of neurites were poor in the case in which a 10/90 culture medium was used. In the case in which the culture medium containing a fetal calf serum of Comparative Example 3 was used, the number of living neurons was small and there existed a considerable number of glial cells.

In order to confirm that the cells cultured were in fact neurons, immunohistochemical staining was performed through use of anti-MAP2 antibody (Boehringer-Mannheim Co.) on the cells cultured with a culture medium containing a culture supernatant and a DMEM/F-12 mixture at a ratio of 75/25 and the cells cultured with a culture medium to which the serum of Comparative Example 3 had been added. Briefly, the culture medium was discarded, and the cells were washed with phosphate buffered saline. Subsequently, the cells were reacted sequentially with 4% p-formaldehyde (Wako Pure Chemical Co., Ltd.) in phosphate buffered saline for 20 minutes, 0.1% Triton X-100 (Boehringer-Mannheim Co.) in phosphate buffered saline for 20 minutes, 1% goat serum in phosphate buffered saline for 20 minutes, and finally with an anti-MAP2 antibody, which had been prepared to have a concentration of 5 $\mu$g/ml with phosphate buffered saline, for 30 minutes. All the reactions were performed at room temperature. Also, after the completion of each reaction, the resultant solution was washed with phosphate buffered saline.

Subsequently, the cells were stained through use of an ABC immunohistochemical staining kit (Vector Co.) and a DAB substrate kit (Vector Co.). Most of the cells that had been determined to be neurons based on their shapes as previously described were stained and were thus confirmed to be neurons. However, the cells that had been incubated with a culture medium containing the serum of Comparative Example 3 were stained in a lower number, and the cells that were considered to be glial cells based on their shapes were not stained.

Example 3 and Comparative Example 4

The procedure of Example 1 was repeated so as to prepare a culture medium for neurons. The sample neurons were obtained from the hippocampus of an embryo of a Wistar rat (16-day-old embryo) and were prepared as described in Example 1. The cells were placed in the wells of a 24-well laminin-coated plate (Sumitomo Bakelite K.K.) (250,000 c/well) and cultured for 14 days. For the initial 3 to 5 days of incubation, cytosine arabinofuranoside (Sigma Co., 5 $\mu$M) was added. One-half the amount of the culture medium was replaced twice each week. In Comparative Example 4, a similar culture was performed through use of a culture medium which had been prepared by adding, to a DMEM/F-12 (1:1) culture medium mixture, insulin (5 $\mu$g/ml), transferrin (5 $\mu$g/ml), progesterone (20 nM), and sodium selenite (20 nM), but not albumin.

The cells were observed on day 14 of culture. All the cells that had been cultured in a culture medium of Comparative Example 4 were dead. However, in the case in which the culture medium of the present invention had been used, network structures were found to be densely formed between neurons.

Example 4

(1) Preparation of a Culture Medium

In a manner similar to that described in Example 1, primary astroglial cells were cultured and culture supernatants were collected. The collected culture supernatants were mixed with a variety of trophic components; i.e., insulin (5 $\mu$g/ml), transferrin (5 $\mu$g/ml), superoxide dismutase (2.5 $\mu$g/ml), catalase (2.5 $\mu$g/ml), sodium selenite (100 nM), progesterone (20 nM), tocopherol acetate (1 $\mu$g/ml), and albumin (2.5 mg/ml) (all by Sigma Co.) so as to prepare a culture medium, and the culture medium was stored at $-70°$ C.

For comparison purposes there were prepared a culture medium composed of the above-mentioned culture supernatants to which no trophic components had been added (same as the composition of Comparative Example 1) and a culture medium composed of the culture supernatants to which some trophic components, i.e., insulin (5 $\mu$g/ml), transferrin (5 $\mu$g/ml), progesterone (20 nM), and sodium selenite (100 nM) had been added but to which albumin had not been added (same as Comparative Example 4).

(2) Culture Test of Neurons

Neuron samples were prepared as follows: The cerebrums of rats (17 days old embryos) were enzymatically treated for 45 minutes at 37° C. with a solution (5 ml) of papain (Worthington Co.) which had been prepared to have a concentration of 20 U/ml through use of phosphate buffered saline containing 1 mM cysteine, 25 mM glucose, and 1 mg/ml albumin (all by Sigma Co.). The enzyme-containing solution was removed, and the cells were dissociated in a DMEM/F-12 culture medium mixture containing gentamicin (50 pg/ml). Subsequently, the cells were centrifugally separated at 700 rpm for 5 minutes. The neurons prepared through use of different culture media of the above-described Examples and Comparative Examples were cultured in a polylysine-coated 48-well plate (Sumitomo Bakelite K.K.) at a cell density of 500 cells/mm$^2$.

After the cells were incubated for 4 days, their morphology was observed under a microscope. The cells that were cultured in a culture medium to which the culture medium of the present invention had been added survived in excellent condition, and exhibited elongated outgrowth of neurites. In contrast, when the culture medium of Comparative Example 1 was used for culture, there were no neurons that survived in satisfactory condition and extended their neurites. In the case in which the culture medium of Comparative Example 2 was used, only some cells were observed. The viability of neurons was determined by use of an MTT (3-4,5-dimethyl-2-thiazolyl)-2,5-diphenyl-2H tetrazolium bromide) cell growth measurement kit (Chemicon International Co.). The viability of the cells cultured with the culture medium of Comparative Example 1 was 5% or less that of the cells cultured with the culture medium of Example 4. Similarly, the viability of the cells cultured with the culture medium of Comparative Example 2 was approximately 20% that of the cells cultured with the culture medium of Example 4. Thus, the culture media of Comparative Examples 1 and 2 provided significantly poor effect as compared to the culture medium of the present invention.

Example 5 and Comparative Example 5

In a manner similar to that described in Example 4, primary astroglial cells were grown and culture supernatants were collected. The collected culture supernatants were mixed with a DMEM/F-12 culture liquid mixture in different ratios (supernatant/culture liquid mixture=75/25, 50/50, 25/75, and 10/90). To the total amount of each mixture were added insulin (5 $\mu$g/ml), transferrin (5 $\mu$g/ml), superoxide dismutase (2.5 $\mu$g/ml), catalase (2.5 $\mu$g/ml), sodium selenite (100 nM), progesterone (20 nM), tocopherol acetate (1 $\mu$g/ml), and albumin (2.5 mg/ml) (all by Sigma Co.) so as to prepare a culture medium. For comparison purposes, a comparative culture medium was prepared by adding fetal calf serum (Hiclone Co.) to a DMEM/F-12 (1:1) mixture in an amount of 10% (same as Comparative Example 3). In a manner similar to that described in Example 1, a neuron suspension was prepared and cultured in a polylysine-coated 24-well plate (Sumitomo Bakelite K.K.) at a cell density of 300 cells/ml.

The cells were observed under a microscope after they were cultured for 4 days. The culture media in which the ratios of culture supernatant to DMEM/F-12 mixture medium were 75/25 and 50/50 both revealed excellent viability of neurons and outgrowth of neurites, though the 75/25 culture medium showed superior results. The 25/75 culture medium showed a smaller number of living cells. No living cells were observed with the 10/90 culture medium. In the case in which the culture medium containing a fetal calf serum of Comparative Example was used, the number of living neurons was small and there existed a considerable number of glial cells.

Example 6 and Comparative Example 6

In a manner similar to that described in Example 4, a culture medium was prepared. For comparison, the culture medium of Comparative Example 3 was used. A neuron suspension was prepared as described in Example 1, and the cells were cultured for 8 days in the wells of a laminin-coated 12-well plate (Sumitomo Bakelite K.K.) at a cell density of 1,200 cells/mm$^2$.

In the case in which the culture medium of the present invention was used, there were observed not only neurons that had been cultured consistently but also cells that were considered to be oligodendroglias from their morphology. In the Comparative Example, only a small number of neurons were observed, and most of the cells observed were considered to be astroglial cells from their morphology.

In order to check the identity of glial cells, immunocytochemical staining was performed through use of anti-GC antibody (Boehringer-Mannheim Co., prepared to 5 µg/ml), anti-GFAP antibody (Boehringer-Mannheim Co., prepared to 8 µg/ml), and anti-A2B5 antibody (Boehringer-Mannheim Co., prepared to 5 µg/ml). The culture medium was discarded, and the cells were washed with phosphate buffered saline. Subsequently, the cells were reacted sequentially with 4% p-formaldehyde (Wako Pure Chemical Co., Ltd.) in phosphate buffered saline for 20 minutes, 0.1% Triton X-100 (Boehringer-Mannheim Co.) in phosphate buffered saline for 20 minutes, 1% goat serum in phosphate buffered saline for 20 minutes, and then with each of the aforementioned antibodies for 30 minutes. For each of 3 species of the antibodies, two wells were used—one well was assigned to represent Example and another well to represent Comparative Example—and thus, a total of 6 wells were used for reaction. The reactions were allowed to proceed at room temperature. The reaction mixtures were independently washed with phosphate buffered saline.

Subsequently, the cells were stained through use of an ABC immunohistochemical staining kit (Vector Co.) and a DAB substrate kit (Vector Co.). The cells that had been cultured with the culture medium of the present invention and had been considered to be oligodendroglias based on their shapes were stained with the anti-GC antibody due to reaction therewith.

However, the cells tested for comparison which had been considered to be astroglial cells based on their shapes were stained with anti-GFAP antibody but not with anti-A2B5 antibody. Therefore, these cells were determined to be type 1 astroglial cells.

INDUSTRIAL UTILITY

When the neuron culture medium of the present invention is used, central nerve cells can be cultured consistently. When they are cultured at a low cell density, neurites extend excellently, and synapses are formed rapidly. On the other hand, when they are cultured at a high cell density, long-term stability of cells that had formed neuronetworks can be obtained. As a result, the culture medium of the present invention enables one to perform neuropharmacological tests, neurotransmission tests, etc. with improved accuracy. Therefore, the culture medium of the invention is useful in studies of dementia, nervous diseases, neurotoxins, etc. as well as elucidation of pathologies in fields such as neuropharmacology and hygiene chemistry.

What is claimed is:

1. A culture medium for neurons comprising (A) a culture supernatant obtained from a culture of primary astroglial cells of a primary passage in a trophic medium supplemented with insulin and transferrin, and (B) albumin.

2. A culture medium for neurons according to claim 1, wherein the trophic medium is further supplemented with selenious acid or a salt thereof.

3. A culture medium for neurons according to claim 1, wherein the trophic medium is a member selected from the group consisting of Eagle's minimum essential medium (MEM), Dulbecco's modified Eagle medium (DMEM), HAM's F-10 medium, HAM's F-12 medium, and a mixture of these media.

4. A culture medium for neurons according to claim 1, wherein progesterone is incorporated in addition to (B) albumin.

5. A culture medium for neurons according to claim 4, wherein a trophic medium is incorparate in the culture supernatant.

6. A culture medium for neurons according to claim 1, wherein, in addition to (B) albumin, there are incorporated progesterone, insulin, transferrin, and selenious acid or a salt of selenious acid.

7. A culture medium for neurons according to claim 1, wherein, in addition to (B) albumin, there are incorporated progesterone, insulin, transferrin, selenious acid or a salt of selenious acid, superoxide dismutase, and catalase.

8. A culture medium for neurons according to claim 1, wherein, in addition to (B) albumin, there are incorporated progesterone, insulin, transferrin, selenious acid or a salt of selenious acid, and an α-tocopherol.

9. A culture medium for neurons according to claim 1, wherein, in addition to (B) albumin, there are incorporated progesterone, insulin, transferrin, selenious acid or a salt of selenious acid, superoxide dismutase, catalase, and an α-tocopherol.

10. A method for culturing neurons comprising incubating neurons in a culture medium for neurons as defined in claim 1.

11. A method for preparing a culture medium for neurons as defined in claim 1, comprising:
   incubating and proliferating primary astroglial cells in a medium supplemented with animal serum,
   culturing the proliferated astroglial cells in a trophic medium supplemented with insulin and transferrin,
   collecting the supernatant of the culture, and
   adding albumin to the collected culture supernatant.

12. A method for preparing a culture medium for neurons as defined in claim 11, wherein selenious acid or a salt thereof is added to the trophic medium.

13. A method for preparing a culture medium for neurons according to claim 11, wherein the trophic medium is a member selected from the group consisting of Eagle's minimum essential medium (MEM), Dulbecco's modified Eagle medium (DMEM), HAM's F-10 medium, HAM's F-12 medium, and a mixture of these media.

14. A method for preparing a culture medium for neurons according to claim 11, wherein progesterone is incorporated in addition to albumin.

15. A method for preparing a culture medium for neurons according to claim 14, wherein a trophic medium is incorporated in the culture supernatant.

16. A method for preparing a culture medium for neurons according to claim 11, wherein, in addition to albumin, there are incorporated progesterone, insulin, transferrin, and selenious acid or a salt of selenious acid.

17. A method for preparing a culture medium for neurons according to claim 11, wherein, in addition to albumin, there are incorporated progesterone, insulin, transferrin, selenious acid or a salt of selenious acid, superoxide dismutase, and catalase.

18. A method for preparing a culture medium for neurons according to claim 11, wherein, in addition to albumin, there are incorporated progesterone, insulin, transferrin, selenious acid or a salt of selenious acid, and an α-tocopherol.

19. A method for preparing a culture medium for neurons according to claim 11, wherein, in addition to albumin, there are incorporated progesterone, insulin, transferrin, selenious acid or a salt of selenious acid, superoxide dismutase, catalase, and an α-tocopherol.

* * * * *

UNITED STATES PATENT AND TRADEMARK OFFICE
CERTIFICATE OF CORRECTION

PATENT NO.    : 6,376,238 B1
DATED         : April 23, 2002
INVENTOR(S)   : Yoshiaki Watanabe It is certified that error appears in the above-identified patent and that said Letters Patent is hereby corrected as shown below:

Column 13,
Line 11, "according to claim 14." should read -- according to claim 11. --

Signed and Sealed this

First Day of April, 2003

JAMES E. ROGAN
*Director of the United States Patent and Trademark Office*